United States Patent [19]

Shimizu et al.

[11] Patent Number: 4,922,205
[45] Date of Patent: May 1, 1990

[54] APPARATUS FOR DETECTING CONTAMINATION ON PROBE SURFACE

[75] Inventors: Kazuo Shimizu, Kashiwa; Hiroshi Amemiya, Kawagoe; Yuichi Sakamoto, Tokyo, all of Japan

[73] Assignee: Rikagaku Kenkyusho, Saitama, Japan

[21] Appl. No.: 363,157

[22] Filed: Jun. 8, 1989

[51] Int. Cl.$^5$ .......................................... G01N 27/60
[52] U.S. Cl. ................................ 324/454; 324/71.1; 324/71.3
[58] Field of Search ...................... 324/454, 71.3, 71.1

[56] References Cited

U.S. PATENT DOCUMENTS 4,006,404  2/1977  Szuszczewicz et al. ............ 324/454
4,023,931  5/1977  Wolfgram ........................ 324/71.1

OTHER PUBLICATIONS

Langmuir and Mott-Smith, Jr., "Studies of Electric Discharges in Gases at Low Pressures", General Electric Review, vol. XXVII, No. 7, Jul. 1924, pp. 449-455.
Wehner and Medicus, "Reliability of Probe Measurements in Hot Cathode Gas Diodes", Journal of Applied Physics, vol. 23, No. 9, Sep. 1952, pp. 1035-1046.

Primary Examiner—Reinhard J. Eisenzopf
Assistant Examiner—Maura K. Regan
Attorney, Agent, or Firm—Brumbaugh, Graves, Donohue & Raymond

[57] ABSTRACT

An apparatus for detecting contamination on probe surface which comprises a sweep voltage generator for generating sweep voltage which is applied to a probe or probes in plasma, a probe current detection circuit for detecting probe current which flows in accordance with the sweep voltage applied, an amplitude discriminator for comparing the probe current with a predetermined threshold and generating an output signal when the probe current becomes equal to the predetermined threshold, a first sample-hold circuit for sampling and holding the sweep voltage upon reception of the output signal from the amplitude discriminator while the sweep voltage is increasing, a second sample-hold circuit for sampling and holding the sweep voltage upon reception of the output signal from the amplitude discriminator while the sweep voltage is decreasing, and a subtracter for providing a difference between the sweep voltages holded in the first and second sample-hold circuit. Degree of the contamination on the probe surface can be evaluated from the difference.

1 Claim, 3 Drawing Sheets

APPARATUS FOR DETECTING CONTAMINATION ON PROBE SURFACE

BACKGROUND OF THE INVENTION

This invention relates to probing apparatus in which a probe electrode is inserted in plasma to pick up various kinds of information of the plasma, and more particularly, to apparatus for detecting degree of contamination on probe surface which is contaminated by ionized materials and so on.

In the field of plasma chemistry, technologies such as property modification and purification of solid surface, synthesis and decomposition of materials and the like have been developed by use of the plasma. In apparatus for such plasma processings, it is very important to accurately pick up information such as ion distribution, electron density and electron temperature in the plasma in order to control plasma conditions with high precision. Probing methods for measuring the various parameters, in which a single probe or a plurality of probes are inserted in the plasma, have been already known. However, since the probes in the plasma are always exposed to an ionized gas, it is gradually contaminated with ionized materials, sputtered materials and so on. The measurement can not be carried out with high accuracy and high precision if the probe surface is contaminated.

Some methods for detecting the degree of the contamination on the surface of the electrode, which will be described hereinafter, have been used.

FIG. 1 shows a circuit diagram for detecting the contamination on the probe surface according to a prior art method. In single probe methods, an electrode $P_1$ is used as the probe electrode and an electrode $P_2$ is used as a reference electrode. In double probe methods, the electrodes $P_1$ and $P_2$, which have the same faculties, are inserted in the plasma. A sweep voltage from a sweep voltage generator 1 is applied between the probe electrodes and then a probe current $I_p$ is detected by a current detecting circuit 2, so that a voltage-current characteristic curve is drawn by a two dimensional display 3 such as a X-Y recorder or an oscilloscope. Typical curves of voltage-current characteristics are shown in FIGS. 2 and 3. FIG. 2 corresponds to the single probe method and FIG. 3 to the double probe method. When the probe surface is not contaminated, the voltage-current characteristic is shown by the curve A or A' in either case of increasing or decreasing of the sweep voltage. On the other hand, when the probe surface is contaminated, a different characteristic is obtained, as indicated by the curves B and C or B' and C'. The curve B and B' corresponds to a characteristic during increasing of the sweep voltage and the curve C and C' to a characteristic during decreasing of the sweep voltage. In other words, when the probe surface is clean, the same characteristic is obtained in either case of increasing or decreasing of the sweep voltage, but when the probe is contaminated, a hysteresis loop is appeared on the probe voltage-current characteristic. Therefore, the contamination of the probe surface have been checked based on whether there is a hysteresis loop on the probe characteristic.

In general, when the probe surface is contaminated, the internal parameters of the plasma, specifically, electron temperature may be overestimated, so that judgement of plasma voltage or estimation of electron density becomes uncertain. Therefore, in the probing methods, cleanness of the probe surface should be secured on the measurements of the inner parameters of the plasma. In order to clean the probe surface, the probe is heated except during the measurements on the internal parameters and the cleanness of the probe surface should be confirmed by the method for detecting the contamination before the measurement of the internal parameters. But since the prior art methods for detecting the contamination spend a few minutes or more when the oscilloscope is used or a few seconds or more when the X-Y recorder is used, the contamination of the probe surface may progress during the measurement of the contamination. In order to detect the contamination at a high-speed based on the prior art methods, expensive apparatus and troublesome manipulations are required.

In brief, an apparatus for rapidly detecting the contamination on the probe surface is required.

SUMMARY OF THE INVENTION

The above requirements are accomplished by this apparatus for detecting contamination on probe surface, which comprises a sweep voltage generator for generating sweep voltage which is applied to a probe or probes in plasma, a probe current detection circuit for detecting probe current which flows in accordance with the sweep voltage applied, an amplitude discriminator for comparing the probe current with a predetermined threshold and generating an output signal when the probe current becomes equal to the predetermined threshold, a first sample-hold circuit for sampling and holding the sweep voltage upon reception of the output signal from the amplitude discriminator while the sweep voltage is increasing, a second sample-hold circuit for sampling and holding the sweep voltage upon reception of the output signal from the amplitude discriminator while the sweep voltage is decreasing, and a subtracter for providing a difference between the sweep voltages held in the first and second sample-hold circuit.

According to this detecting apparatus, it becomes easy to decrease the measurement time below one-thousandth of a second and the contamination due to the cleanness measurement is negligible. Whenever the contamination on the probe surface is detected, processes for eliminating the contamination and reexamination of the cleanness are required. In such reexamination, the effects of this invention are much more displayed.

PREFERRED EMBODIMENT OF THE INVENTION

Figure 1:
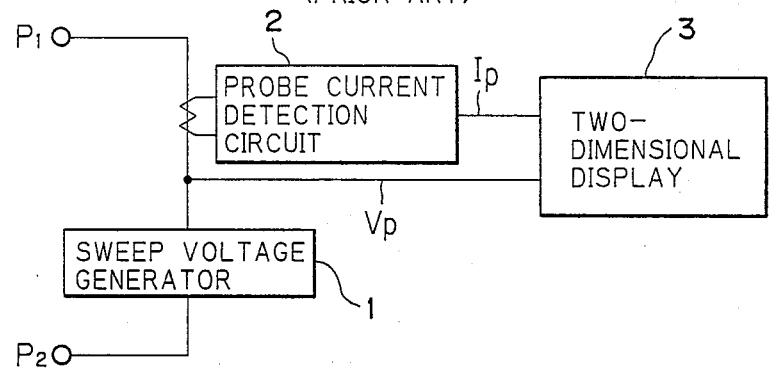
FIG. 1 is a circuit diagram for examining the contamination on the probe surface according to a prior art method.
Figure 2:
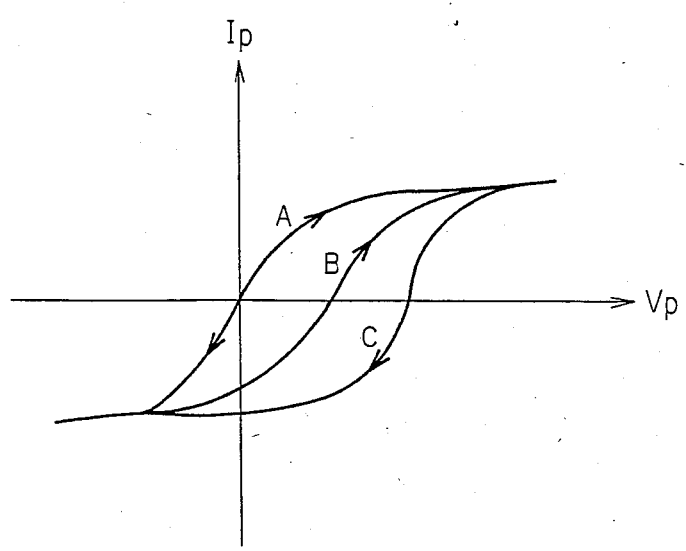
FIG. 2 is a graph showing a voltage-current probe characteristic when double probes are used.
Figure 3:
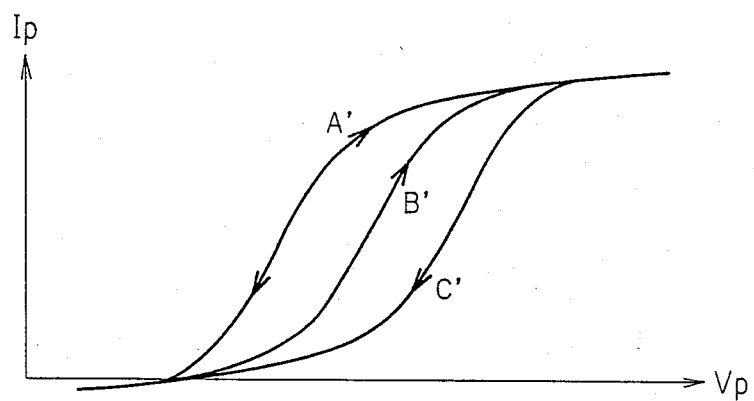
FIG. 3 is a graph showing a voltage-current probe characteristic when a single probe is used.
Figure 5:
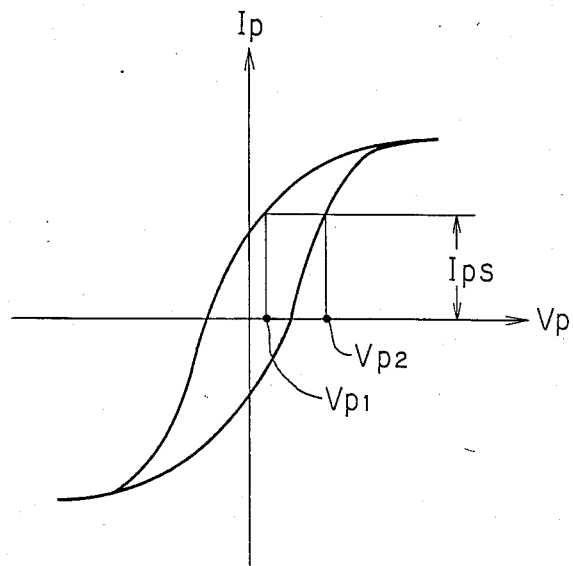
FIG. 5 is a graph showing a probe characteristic when the probe surface is contaminated.
Figure 4:
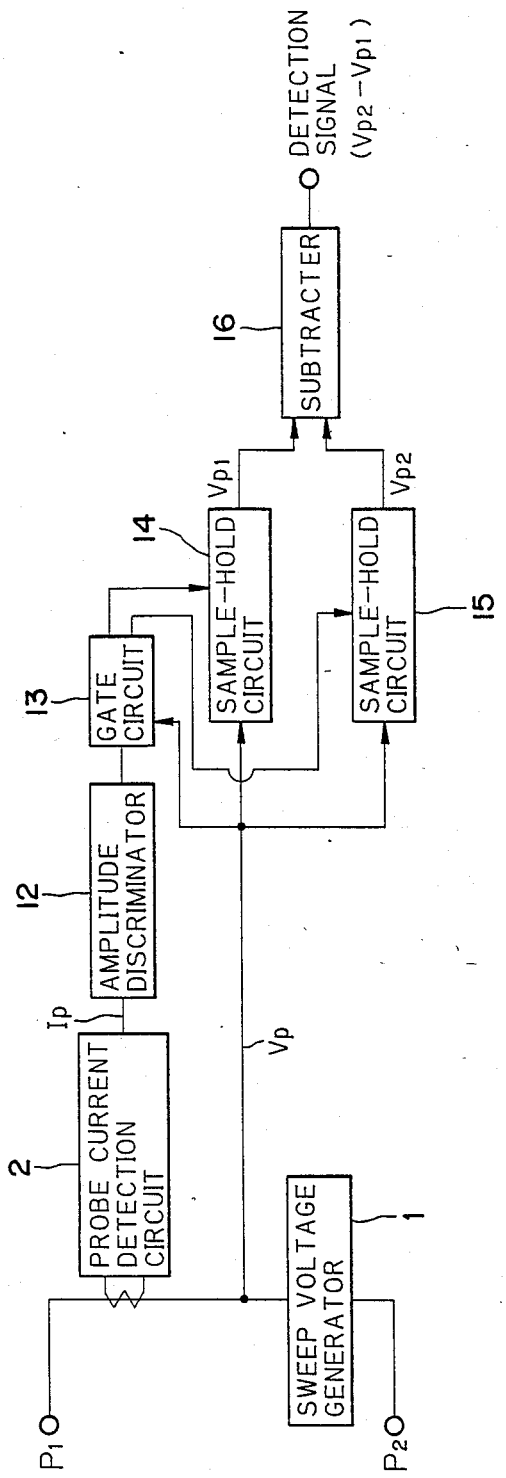
FIG. 4 is a circuit diagram showing an example of this invention.

FIG. 4 is a circuit diagram showing an example of this invention. A sweep voltage generator 1 generates sweep voltage $V_p$ of a triangle waveform. When the sweep voltage $V_p$ is applied to probe electrode $P_1$ and $P_2$, probe current $I_p$ flows. This probe current $I_p$ is detected by a probe current detection circuit 2 and the detected probe current is provided to an amplitude discriminator 12. This amplitude discriminator 12 compares the detected probe current $I_p$ with a predetermined threshold $I_{ps}$ and generates a pulse when the values $I_p$ and $I_{ps}$ equal each other. The two sample-hold circuits 14 and 15 both sample the sweep voltage upon reception of a sampling pulse and hold the sampled sweep voltage. The gate circuit 13 directs the pulse from the amplitude discriminator 12 as the sampling pulse to the sample-hold circuit 14 when the sweep voltage is increasing or to the sample-hold circuit 15 when the sweep voltage is decreasing. In FIG. 5, there is shown a relation between the sweep voltage $V_p$ and the probe current threshold $I_{ps}$. When the probe current $I_p$ increases to the threshold $I_{ps}$ while the sweep voltage is increasing, the sample-hold circuit 14 holds the sweep voltage $V_{p1}$ and when the probe current reaches to the threshold $I_{ps}$ again while the sweep voltage is decreasing, the sample-hold circuit 15 holds the sweep voltage $V_{p2}$. A subtracter 16 gives a difference between the held sweep voltage $V_{p2}$ and $V_{p1}$. Therefore, if the probe surface is contaminated to exhibit a hysteresis in the probe characteristic, a detection signal $V_{p2}-V_{p1}$ is provided. From the difference, the degree of the contamination on the probe surface can be evaluated.

Although this invention has been described in its preferred form, it will be apparent to those skilled in the art that various modification and variations can be made without departing from the spirit or scope of this invention.

What is claimed is:

1. An apparatus for detecting contamination on probe surface comprising:
    a sweep voltage generator for generating sweep voltage which is applied to a probe or probes in plasma,
    a probe current detection circuit for detecting probe current which flows in accordance with the sweep voltage applied,
    an amplitude discriminator for comparing the probe current with a predetermined threshold and generating an output signal when the probe current becomes equal to the predetermined threshold,
    a first sample-hold circuit for sampling and holding the sweep voltage upon reception of the output signal from the amplitude discriminator while the sweep voltage is increasing,
    a second sample-hold circuit for sampling and holding the sweep voltage upon reception of the output signal from the amplitude discriminator while the sweep voltage is decreasing, and
    a subtracter for providing a difference between the sweep voltages held in the first and second sample-hold circuit.

* * * * *